United States Patent
Ning

(10) Patent No.: US 6,618,466 B1
(45) Date of Patent: Sep. 9, 2003

(54) APPARATUS AND METHOD FOR X-RAY SCATTER REDUCTION AND CORRECTION FOR FAN BEAM CT AND CONE BEAM VOLUME CT

(75) Inventor: Ruola Ning, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/078,529

(22) Filed: Feb. 21, 2002

(51) Int. Cl.⁷ .......................... A61B 6/00; G01N 23/083
(52) U.S. Cl. .................. 378/62; 378/7; 378/98.4; 378/901
(58) Field of Search ................ 378/4, 7, 15, 62, 378/98, 98.4, 901

(56) References Cited

U.S. PATENT DOCUMENTS

| | | | |
|---|---|---|---|
| 5,533,088 A | * 7/1996 | Fivez | 378/98.4 |
| 5,999,587 A | 12/1999 | Ning et al. | |
| 6,052,433 A | * 4/2000 | Chao | 378/98.9 |
| 6,075,836 A | 6/2000 | Ning | |
| 6,134,297 A | * 10/2000 | Chao | 378/98.12 |
| 6,298,110 B1 | 10/2001 | Ning | |

FOREIGN PATENT DOCUMENTS

| WO | WO 99/01066 | 1/1999 |
|---|---|---|
| WO | WO 01/35829 A1 | 5/2001 |
| WO | WO 02/30282 A2 | 4/2002 |

OTHER PUBLICATIONS

Carlson, Blake, "Homework 2: Image Interpolation and Filtering," pp. 1–19, Advanced Image Processing, www.engineering.uiowa.edu/~gec/248_students/blake_carlson/hw2, Mar. 8, 2000.

* cited by examiner

Primary Examiner—David V. Bruce
(74) Attorney, Agent, or Firm—Blank Rome, LLP

(57) ABSTRACT

In cone-beam volume computed tomography or similar imaging techniques, the effects of x-ray scatter are reduced through using a beam compensation filter (a bow tie filter), air gap technique, and an antiscatter grid and corrected through the use of a beam stop array combined with interpolation or convolution operation. Images are taken with the beam stop array, and a larger number of images are taken without the beam stop array. The images taken with the beam stop array are spatially interpolated to derive scatter information, which is then angularly interpolated to provide as many scatter images as there are images taken without the beam stop array. The interpolations are performed through cubic spline interpolation or any other interpolation techniques or low-pass filtering operation (convolution operation with a selected kernel). Each scatter image is subtracted from a corresponding one of the images taken without the beam stop array to provide a sequence of scatter-corrected images.

35 Claims, 3 Drawing Sheets

APPARATUS AND METHOD FOR X-RAY SCATTER REDUCTION AND CORRECTION FOR FAN BEAM CT AND CONE BEAM VOLUME CT

STATEMENT OF GOVERNMENT INTEREST

The present invention was developed with the support of NIH Grant Nos. 2R01HL48603 and IR01CA85904-01. The government has certain rights in the present invention.

FIELD OF THE INVENTION

The present invention is directed to a system and method for reduction of x-ray scatter in imaging systems and more particularly to such a system and method which use both spatial and temporal interpolation for such reduction. The present invention is usable with several imaging techniques, including fan beam and cone beam CT.

DESCRIPTION OF RELATED ART

Scatter reduction and correction are required for both medical (e.g., clinical, small animal imaging) and nonmedical imagine applications (e.g., explosive detection, nondestructive testing, industrial imagine guided manufacturing applications). Compton scatter interaction always exists in the x-ray energy range useful for imaging (10 keV to a few MeV). In some segments of the x-ray spectrum, X-ray scatter interaction is dominant. For example, within the effective energy range of medical diagnostic CT (60–80 keV), it is recognized that the Compton interaction (>80%) plays a predominant role over photoelectrical interaction (<10%) and coherent interaction (<5%) when x-ray photons pass through water-like soft tissues, although slightly higher percentages for both of them are observed when x-ray photons pass through compact bone. However, scatter intensity detected by a detector usually contributes to noise, not to a useful signal for imaging. Therefore, scatter reduction and correction are required to improve reconstruction accuracy of linear attenuation coefficient (LAC) distribution for both medical (clinical, small animal imaging and nonmedical imagine applications (explosive detection, nondestructive testing, industrial imagine guided manufacturing applications).

Before the mechanism in which x-ray scatter interferes with cone beam volume computed tomography (CBVCT) imaging is described, it is instructive to know how x-ray scattering deteriorates the quality of projection imaging. FIG. 1A shows an example in which a disc 102 is embedded in a uniform cylindrical object 104 whose LAC is slightly larger than that of the disc 102. If the object 104 is disposed in a cone beam C emitted by a cone-beam source 106, and the cone beam C is then received by a detector 108, a projection image is acquired as shown in FIG. 1B. Due to the LAC discrepancy, the number of x-ray photons detected in the area corresponding to the disc is $N+\Delta N$, but that detected in the background area is N, with no x-ray photons scattered. By limiting to an additive-noise-free situation, the ability to visualize such a structure is generally evaluated by contrast, which is defined as $$C = \frac{N + \Delta N - N}{N} = \frac{\Delta N}{N} \quad (1)$$

It is known that the flux of x-ray photons observes the Poisson distribution, while the transmittance of x-ray photons through an object observes the binomial distribution. The cascading of a Poisson process and a binomial process is still a Poisson process. Hence, if the mean number of the x-ray photons transmitting the disc and its surrounding area are $N+\Delta N$ and N respectively, their corresponding standard deviations are $\sqrt{N+\Delta N}$ and $\sqrt{N}$. From the perspective of system analysis, the scattered x-ray photons behave like additive noise. In digital projection imaging where the display window of an ROI (region of interest) can be adjusted arbitrarily, the ability to visualize such a local structure is more appropriately measured by SNR (signal-to-noise ratio), which is defined as $$SNR = \frac{N + \Delta N - N}{\sqrt{N}} = \frac{\Delta N}{\sqrt{N}} = C\sqrt{N} \quad (2)$$

On the other hand, letting the mean number of the scattered x-ray photons be $N_s$, the scatter-to-primary ratio (SPR) is defined as $$SPR = \frac{N_s}{N} \quad (3)$$

and the scatter degradation factor (SDF) is defined as $$SDF = \frac{N}{N + N_s} = \frac{1}{1 + N_s/N} = \frac{1}{1 + SPR} \quad (4)$$

Consequently, (1) and (2) respectively degrade to $$C_s = \frac{N + N_s + \Delta N - (N + N_s)}{N + N_s} = \frac{\Delta N}{N + N_s} = \frac{C}{1 + N_s/N} = SDF \cdot C \quad (5)$$

$$SNR_s = \frac{N + N_s + \Delta N - (N + N_s)}{\sqrt{N + N_s}} = \frac{\Delta N}{\sqrt{N + N_s}} = \frac{SNR}{\sqrt{1 + N_s/N}} = \sqrt{SDF} \cdot SNR \quad (6)$$

in the presence of x-ray scatter. In other words, due to scattered x-ray photons, the local contrast and SNR of the structure are deteriorated by the factors of SDF and $\sqrt{SDF}$ in a projection image, respectively.

Suppose that $I_p(i,j)(i \in I, j \in J)$ refers to the image formed by the primary x-ray photons, and $I_s(i,j)(i \in I, j \in J)$ the image formed by the scattered photons, where I and J are the vertical and horizontal dimension of a projection image. As a result, a 2D SPR distribution is defined as $$SPR(i, j) = \frac{I_s(i, j)}{I_p(i, j)} \quad (i \in I, j \in J) \quad (7)$$

and subsequently $$SDF(i, j) = \frac{1}{1 + SPR(i, j)} \quad (i \in I, j \in J) \quad (8)$$

It has been found that, given an object, the distribution of $I_s(i,j)$ is dependent on its structure, thickness and field of view (FOV) through which $I_p(i,j)$ is formed. However, regardless of how the distribution of $I_p(i,j)$ fluctuates, the variation of $I_s(i,j)$ is so smooth that it can be approximately treated as a 2D spatial low-pass filtering of $I_p(i,J)$, and several low-pass filtering models associated with different filter kernels have been proposed. That means that a strong spatial correlation exists between neighboring pixels.

Intuitively, scatter distribution in each projection image can be recovered from its spatial samples using either interpolation methods, such as cubic spline interpolation or bi-linear interpolation methods, or a convolution operation with a selected convolution kernel (a low pass filtering in the frequency domain).

On the other hand, the SPR(i,j) or SDF(i,j) usually fluctuates very much, especially where $I_p$(i,j) is relatively low. Hence, the SPR(i,j) or SDF(i,j) is usually taken into account to reflect the severity of the x-ray scatter in projection imaging.

A CBVCT (cone beam volume computed tomography) image is reconstructed from a set of consecutive 2D projection images that are sequentially acquired. Intrinsically, the x-ray scatter interferes with the X-ray transform non-linearly. Once the X-ray transform is acquired, the artifact caused by the x-ray scatter in a tomographic image is reconstruction-algorithm-dependent. Thus, the experimental investigation of the x-ray scatter artifact in tomographic imaging is preferable in practice. In conventional CT (computed tomography), due to the adoption of a slit collimator, the severity of the longitudinally scattered x-ray photons is reduced to a secondary order in comparison to that of the transversely scattered ones. To further reduce the transversely scattered x-ray, other measures, such as the bow-tie x-ray attenuator, and the post-patient out-of-slice collimator used in a $3^{rd}$-generation CT or the reference detector used in a $4^{th}$-generation CT, are usually taken into account.

Unfortunately, for CBVCT, the slit collimator has to be removed to fully use the generated cone shaped x-ray beam. Hence, much more severe x-ray scatter interference is expected in CBVCT, although the air gap technique and beam-shaping (bow-tie) attenuator are still useful for reducing scatter. Supposing $I_p$(x,y) refers to the projection image formed by primary x-ray photons, and $I_s$(x,y) that formed by scattered x-ray photons, we have $$I_t(x,y)=I_p(x,y)+I_s(x,y) \tag{9}$$

As a result, a 2D SPR distribution is defined as $$SPR(x,y) = \frac{I_s(x,y)}{I_p(x,y)} \tag{10}$$

By substituting (10) into (9), one gets $$I_t(x,y)=I_p(x,y)[1.0+SPR(x,y)] \tag{11}$$

Furthermore, by taking the incident x-ray intensity distribution $I_0$(x,y) into account and applying logarithm, we get the X-ray transform data for CB reconstruction $$P(x,y) = \ln\frac{I_0(x,y)}{I_t(x,y)} = \ln\frac{I_0(x,y)}{I_p(x,y)[1.0+SPR(x,y)]} = \tag{12}$$
$$\ln\frac{I_0(x,y)}{I_p(x,y)} - \ln[1.0+SPR(x,y)] \equiv P_p(x,y) + P_s(x,y)$$

where $$P_p(x,y) = \ln\frac{I_0(x,y)}{I_p(x,y)} \tag{13}$$

are the X-ray transform distribution corresponding to primary and scattered x-ray photons respectively. Hence, due to scatter interference, the CB reconstruction of an object becomes $$f(\vec{r})+\Delta f(\vec{r}) \tag{15}$$

i.e., the sum of the CB reconstruction corresponding to the projection image formed by primary x-ray photons and that formed by scattered ones.

Inferred from what is presented above, it is not difficult to obtain the following important observations concerning the reconstruction error introduced by x-ray scatter (RE) in CBVCT:

- $I_s$(x,y) is the source of Re;
- RE is determined by SPR distribution $-\ln[1.0+SPR(x,y)]$, rather than merely $I_s$(x,y). In other words, RE is determined by not only $I_s$(x,y) but also $I_p$(x,y);
- RE is always negative because $-\ln[1.0+SPR(x,y)]$ is less than zero. This is the rationale behind the cupping effect or shading effect in CBVCT images;
- While SPR(x,y)>>1, i.e., the x-ray scatter interference is extraordinarily severe, RE is equivalently proportional to $-\ln$ SPR(x,y);
- While SPR(x,y)<<1, i.e., the x-ray scatter interference is moderate, RE is equivalently proportional to $-$SPR(x,y);
- The RE caused by x-ray scatter interference can be alleviated through two approaches: (a) reducing $I_s$(x,y); (b) increasing $I_p$(x,y); and
- It should be emphasized that a significant drop in intensity of $I_p$(x,y) formed by primary x-ray photons is to be avoided in practice because the resultant increase in $-\ln[1.0+SPR(x,y)]$ can be extremely high and results in severe RE in CBVCT.

The simplest approach to suppress x-ray scatter is the air gap, which has been employed in projection imaging, particularly chest radiography, for many years. A CBVCT inherits the air gap approach due to the distance maintained between x-ray detector and the object to be scanned. As illustrated in FIG. 2, T represents the thickness of the object 202 to be imaged, $x_p$ the distance between the primary source (PS) 204 and the exit surface of the object 202, and $x_a$ the distance between the exit surface and the x-ray receptor 206 (air gap). All the scattered x-ray photons could be assumed to originate from an effective scatter point source (ESPS) 208 at an $x_s$ distance from the exit surface of the object 202.

Governed by the inverse-square-law, both the primary and scattered x-ray flux are attenuated by an air gap. However, for a wide range of experimental conditions, such as the phantom thickness, FOV, x-ray source energy as well as the distance $x_p$ between the x-ray focal spot and the exit surface of the phantom, $x_s$ is consistently within the range of 15~20 cm and usually much shorter than $x_p$. Consequently, the scattered x-ray photons are attenuated by an air gap to an extent larger than that of the primary x-ray photons. This means that, given an air gap within a reasonable range, more scattered x-ray photons are selectively attenuated by an air gap, thus improving SPR. A formula to get the optimal $x_a$ is $$x_{a\_opt} = \frac{1}{2}(x_t - x_s) \tag{16}$$

where $x_t$ is the allowable distance between the x-ray source focal spot and the receptor.

In conventional CT, the primary function of a bow-tie attenuator is to ameliorate the quality of the x-ray source, so that the artifact caused by beam hardening can be reduced. Another important function is to alleviate the requirement on the dynamic range of an x-ray detector and lower the radiation dose to a patient. Particularly, the SPR uniformity of a cylindrical object is improved, since the bow-tie attenuator compensates for the primary x-ray photon distribution non-uniformity, so that the cupping artifact in reconstructed images can be significantly reduced.

Another approach to suppress x-ray scatter is the antiscatter grid, which is either linearly or crosswise focused. The linearly focused grid provides an inclusive performance better than that of the crosswise focused grid. In practice, the focal spot of an x-ray source is positioned on the convergent line of a linear grid that is perpendicular to the central beam emanating from the focal spot, so that most of the primary x-ray photons can transmit the interspaces. Since scattered x-ray photons behave as if they originated from its ESPS, most of them are attenuated by a linear grid. Generally, the larger the grid ratio, the more selective the attenuation. However, a grid with too high a ratio absorbs too many primary x-ray photons, resulting in an increased x-ray tube loading and exposure to the patient. Moreover, it was observed that the performance of both the air gap approach and the grid approach is strongly dependent on x-ray scatter. Whereas for high x-ray scatter both provide comparable improvement on SNR, for low to moderate situations an air gap definitely performs better. Furthermore, if x-ray scatter is very low(SPR<0.7), a grid even degrades SNR due to the absorption of primary x-ray photons by the grid. Therefore, for SPR<0.7, an antiscatter grid may not be used. For example, in cone beam volume CT breast imaging (CBVCT mammography) an antiscatter grid may not be used.

The other approach involves the use of a beam stop (BS) array. As shown in FIGS. 3A and 3B, an x-ray BS array 302 having small lead discs 304 is placed between the x-ray source 306 and the object to be imaged, which in an illustrative example is a phantom 308 on a table 310. On the far side of the phantom 308 from the source 306 is a detector 312. By adequately choosing the dimensions of the lead discs 304, each shadowed area in a projection image is as small as possible, while an entire block of the primary x-ray photons is assured. The small lead discs are deployed in an array with an orthogonal distance significantly larger than the diameter of small lead disc, so that the shadows are apart from each other. A total of two projection images—one with the beam stop array (image I) and the other without it (image II)—are taken. The intensity detected within each shadowed area in image II is assumed to be exclusively that of the scattered x-ray photons, resulting in the x-ray scatter distribution sampled on a sparse lattice. Employing a spatial cubic spline interpolation (or bilinear interpolation) on these samples, the scatter distribution (scatter image) is estimated. Subsequently, the scatter image is subtracted from image I to get the image exclusively formed by the primary x-ray photons (primary image).

The merit of the BS array approach is its ability of adaptively removing scattered x-ray intensity. Nevertheless, if it were directly employed in CBVCT, the resultant exposure would be doubled, and such a doubled exposure is definitely undesirable in practice.

The inventor's previous work disclosed in WO 01/35829, published May 25, 2001, whose disclosure is hereby incorporated by reference in its entirety into the present disclosure, discloses a technique using a BS array in which the scaling factors for estimating scatter distribution and the convolution kernels at sampled angle positions can be determined. Then the scatter distributions are estimated using the convolution kernel at corresponding angle positions and subtracted from the detected positions. However, that technique requires determination of the convolution kernels, rather than the use of existing kernels for cubic spline interpolation. It also depends on compression of the patient's breast into a cylindrical shape, which is not always desirable or even possible for any given object to be imaged.

SUMMARY AND OBJECTS OF THE INVENTION

It will be apparent from the above that a need exists in the art to improve the reconstruction accuracy in CBVCT without adversely affecting patient safety and without adversely reducing data acquisition speed. It is therefore an object of the present invention to reduce the x-ray scatter interference.

It is another object of the invention to reduce the x-ray scatter interference in CBVCT to a clinically acceptable level.

It is further object of the invention to reduce the x-ray scatter interference in CBVCT to improve reconstruction accuracy of CBVCT.

It is a still further object of the invention to reduce the x-ray scatter interference in CBVCT without the use of excessive additional x-ray exposure to the patient or, more generally, to the object to be imaged.

It is a still further object of the invention to reduce the number of images to be taken with the BS array without requiring the determination of convolution kernels at sampled angle positions.

It is a still further object of the invention to reduce the number of images to be taken with the BS array, regardless of the ability to compress the object to be imaged into any particular shape.

It is a still further object of the invention to combine the following techniques together to combat scatter interference in CBVCT: x-ray beam compensation filter (bow-tie filter), air gap technique, and antiscatter grid to reduce detected scatter, and an image processing technique for final scatter correction to improve reconstruction accuracy.

To achieve the above and other objects, the present invention is directed to a system and method for imaging in which the x-ray scatter interference is reduced through the decomposition of primary and scatter image subsequences. From the perspective of image sequence processing, all the consecutively acquired projection images constitute an image sequence that includes a primary image subsequence (PIS) needed by CB reconstruction and a scatter image subsequence (SIS) interfering with CB reconstruction. The inventor has found that the spatial fluctuation of the SIS is significantly less intense than that of the PIS, indicating that a considerable spatial correlation exists in the former. Hence, it is possible to recover an SIS from samples acquired at a very low sampling rate using the BS array technique, and then its associated PIS can be obtained by correspondingly subtracting the SIS from the projection image sequence. The sampling rate of an SIS could be so low, e.g., 1, to 2/rotation 4/rotation, that its samples can be obtained in a way similar to the acquisition of scout localization images, which is usually employed in conventional/spiral CT to prescribe scan location relative to anatomic landmarks. Consequently, the resultant extra exposure and extra acquisition time would be acceptable. Again, the cubic spline interpolation or bilinear interpolation is angularly used to recover an SIS from its samples.

Theoretical and experimental investigations conducted by the inventor reveal that the anti-scatter approaches inherited from projection imaging, such as the air gap, beam-shaping attenuator and linear anti-scatter grid, can substantially reduce cupping/shading distortion (LAC reconstruction inaccuracy) in a CBVCT image caused by x-ray scatter interference, and so does the present invention. The quantitative performance evaluation of the present invention carried out using the scatter phantom shows that its capability of adaptively suppressing x-ray scatter interference in CBVCT imaging is still satisfactory even at an AI (angular interval) of 90°, which is equivalent to the acquisition of only 4 extra projection images with the BS array installed. This means that the present invention provides a novel and effective approach to combat x-ray scatter interference in CBVCT, and the extra x-ray exposure induced by it is definitely tolerable in practice.

A particular embodiment of the present invention provides a hybrid method by optimally combining the following techniques (discussed above) together to combat scatter interference: an x-ray beam compensation filter (bow-tie filter), an air gap technique, an antiscatter grid to reduce detected scatter, and an image processing technique for final scatter correction to improve reconstruction accuracy.

Finally, the penumbra phenomena resulting from the finite focal spot of an x-ray tube disturbs an accurate sampling of the distribution formed by scattered x-ray photons. Calibration can be used in practice to alleviate, if not eliminate, such a disturbance as much as possible.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1A:
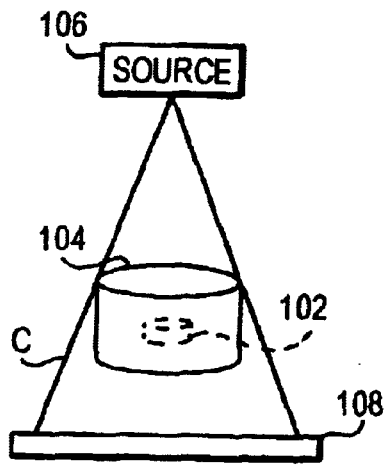
FIGS. 1A and 1B show a basic example of scatter in the prior art.
Figure 1B:
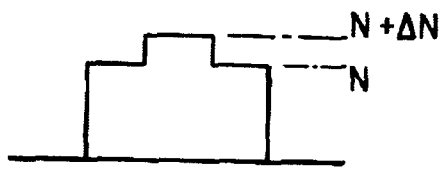
Figure 2:
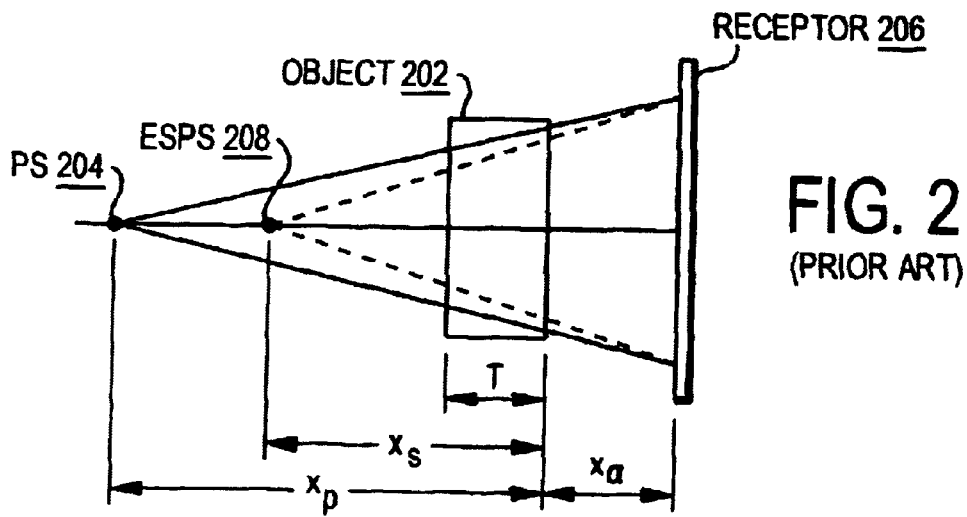
FIG. 2 shows an example of an air-gap technique used to reduce the effects of scatter in the prior art.

A preferred embodiment of the present invention will now be set forth in detail with reference to the drawings, in which like reference numerals refer to like elements or steps throughout.

The preferred embodiment combines the x-ray beam compensation filter (bow-tie filter), the air gap technique, an antiscatter grid and the scatter correction algorithm to be described below to reduce and correct for scatter. Therefore, a preferred system configuration includes an x-ray tube for producing a cone-shaped x-ray beam, a bow-tie filter, an antiscatter grid in the front of a 2D detector, the 2D detector itself and a computer system to control the system and process the two sets of projections to obtain scatter-corrected projections and reconstruct 3D images from a set of scatter-corrected projections. This system should have two versions: one with a beam stop array (BSA) in place and another without the BSA.

Figure 4:
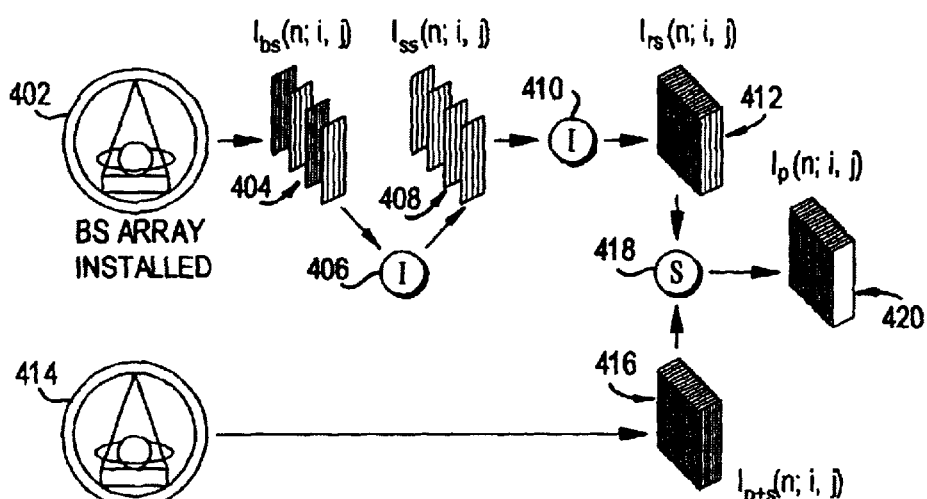
FIG. 4 shows a flow chart of a preferred embodiment of the present invention.

The technique used in the preferred embodiment will be referred to as scatter correction algorithm (SCA)). The implementation of the SCA is plotted in FIG. 4, where I represents cubic spline interpolation, and S, subtracting each frame of an image sequence correspondingly from that of another image sequence. The 1st I operation is spatially implemented, but the 2nd I operation is angularly implemented. For lucidity, the following definitions of image sequences in FIG. 4 are listed, where (I,J) is the image dimension, and N'<N.

$I_{p+s}(n;i,j)$, (n∈N): the projection image sequence;

$I_p(n;i,j)$, (n∈N): the PIS contained in the projection image sequence;

$I_s(n;i,j)$, (n∈N): the SIS contained in the projection sequence;

$I_{bs}(n;i,j)$, (n∈N'): the projection image subsequence acquired using the BS array technique;

$I_{ss}(n;i,j)$, (n∈N): the samples of SIS obtained from $I_{bs}(n;i,j)$ by spatial I operation;

$I_{rs}(n;i,j)$ (n∈N): the SIS recovered from $I_{ss}(n;i,j)$ by angular interpolatin I operation.

Figure 3A:
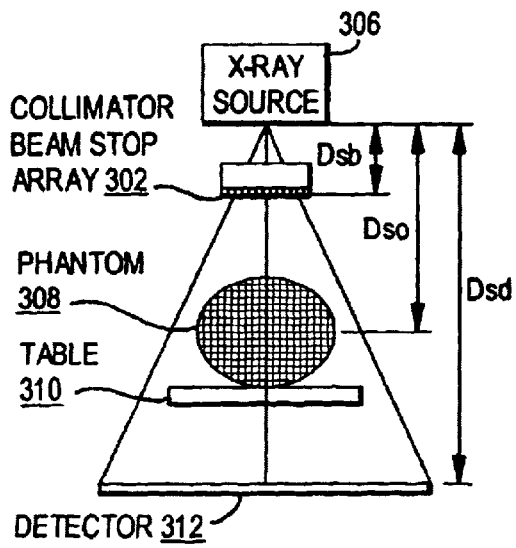
FIGS. 3A and 3B show an example of a beam stop array technique used to reduce the effects of scatter in the prior art.
Figure 3B:
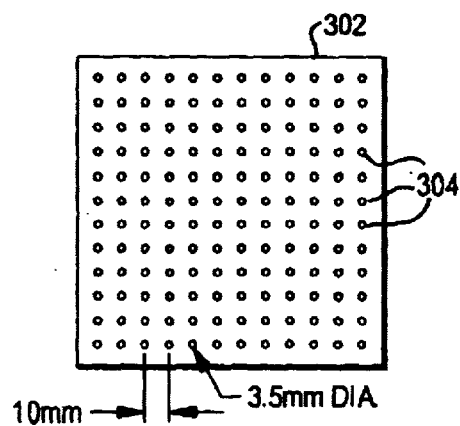

More specifically, as shown in FIG. 4, N' images are taken at step 402 using a beam stop array like that of FIGS. 3A and 3B, thereby providing the $I_{bs}$ image sequence 404. A spatial I operation at step 406 provides the $I_{ss}$ image sequence at step 408. Since that image sequence has only N' images rather than N, an angular interpolation I operation is performed at step 410 to provide the $I_{rs}$ image sequence, which has N images, at step 412.

At step 414, N images are taken without the beam stop array to provide the $I_{p+s}$ image sequence at step 416. At step 418, each $I_{rs}$ image is subtracted from the corresponding $I_{p+s}$ image to provide the $I_p$ image sequence at step 420. Either or both of the I operations can be replaced by convolution using a suitable kernel such as a low-pass filter or by any other suitable technique.

Theoretically, $$I_p(n;i,j)=I_{p+s}(n;i,j)-I_s(n;i,j). \qquad (17)$$

However, only $I_{rs}(n;i,j)$, an estimation of $I_s(n;i,j)$, is available in practice using the SCA. Given the definition of exposure increase factor $$EIF = 100\% \cdot \frac{N'}{N}, \qquad (18)$$

the success of SCA is dependent on the accuracy of $I_{rs}(n;i,j)$ as an estimation of $I_s(n;i,j)$ while EIF is within an acceptable threshold.

Moreover, the relative reconstruction error (RRE) is defined as:

$$RRE = 100\% \cdot \sqrt{\frac{1}{I \cdot J} \sum_{i=0}^{I-1} \sum_{j=0}^{J-1} \left( \frac{\vec{I}_{rs}(i,j) - \vec{I}_s(i,j)}{\vec{I}_s(i,j)} \right)^2}, \qquad (19)$$

where $\vec{I}_{rs}(i,j)$ is the central slice image reconstructed from the scatter-corrected projections generated by using angular interpolation of angularly-sampled SIS, and $\vec{I}_s(i,j)$ is the central slice image reconstructed from the scatter-corrected projections generated by using a complete SIS.

Figure 5:
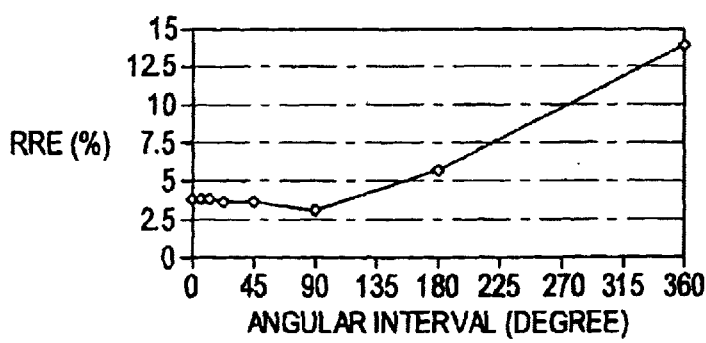
FIG. 5 shows reconstruction error as a finction of angular interval.

The LAC reconstruction error of the scatter phantom as a function of AI in the application of SCA has been investigated. The result is illustrated in FIG. 5, which shows the LAC reconstruction error as a function of AI employed in the application of SCA. FIG. 5 shows that the LAC reconstruction accuracy is acceptable while the AI is no larger than 90°. Notice that, however, little improvement in LAC reconstruction accuracy can be obtained when the AI in the application of SCA is smaller than 90°.

In a volume CT, a direct reconstruction of an object can be obtained. A system for doing so will now be disclosed. The system is based on that disclosed in U.S. Pat. No. 5,999,587, issued Dec. 7, 1999, whose disclosure is hereby incorporated by reference in its entirety into the present disclosure.

Figure 6A:
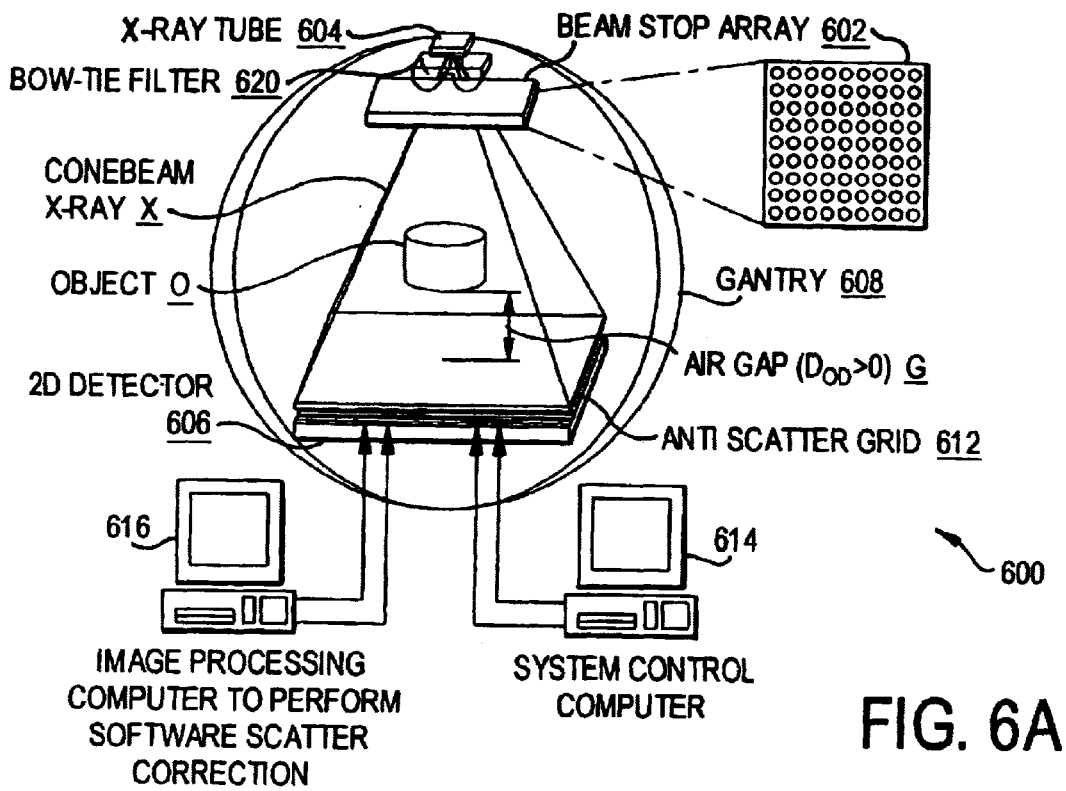
FIGS. 6A and 6B shows an apparatus on which the preferred embodiment can be implemented.
Figure 6B:
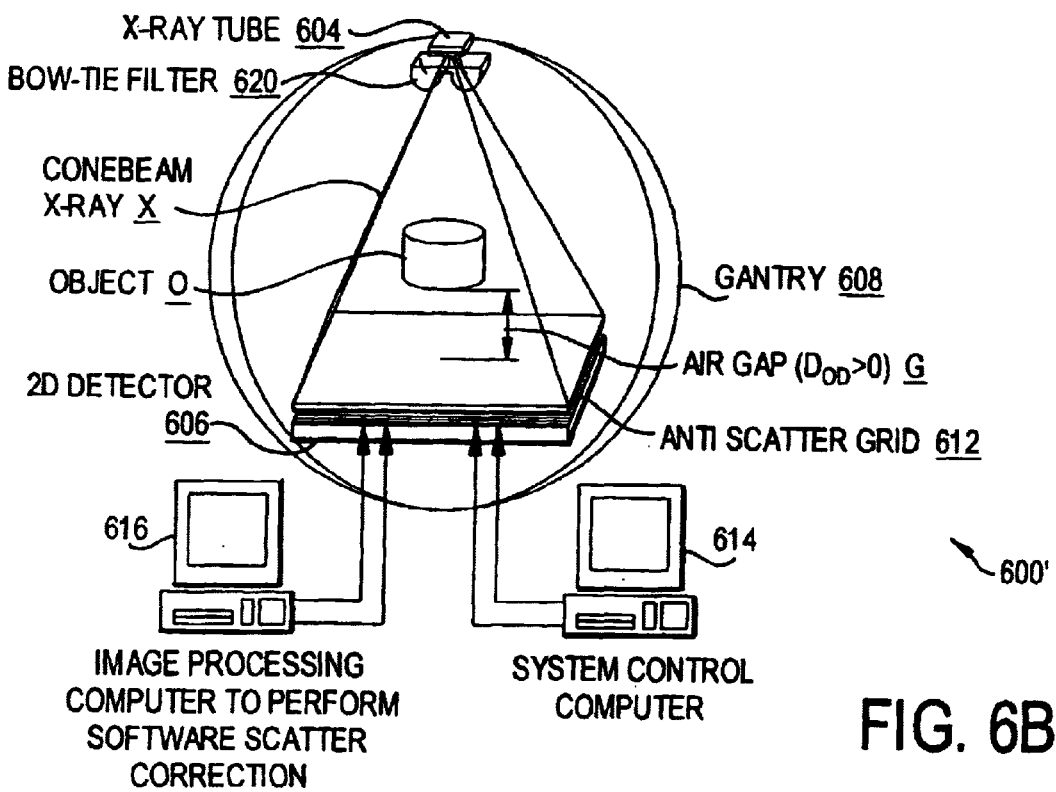

Referring now to FIGS. 6A and 6B, it is shown how the cone-beam tomography system 600, 600' of the preferred embodiment can be used to obtain a direct 3-D reconstruction of an object. The volume CT scanning apparatus 600, 600'is illustrated in a simplified block diagram form. The invention may preferably be employed in conjunction with such a volume CT scanning apparatus to generate a 3-D reconstruction matrix of the object. Based on the 3-D reconstruction matrix, the desired three dimensional display can be obtained. The difference between the apparatus 600 of FIG. 6A and the apparatus 600'of FIG. 6B is that the apparatus 600 of FIG. 6A includes a beam stop array 602 like that of FIGS. 3A and 3B.

A volume CT scanning apparatus examines an object O (which may be a human or animal patient or an inanimate object) using a cone shaped radiation beam X which traverses a set of paths across theobject O. An x-ray source 604 and a 2-D detector 606 are mounted on a gantry frame 608 that rotates around the object O being examined. The operating voltage for the x-ray source is obtained from a conventional high-voltage generator (not shown) in such a manner that the x-ray source 604 produces the desired cone-shaped beam of radiation when the high-voltage is applied to it. Also provided are a bow-tie filter 610, the above-mentioned beam stop array 602, and an anti-scatter grid 612. An air gap G having a non-zero dimension $D_{OD}$ is provided between the bottom of the object O and the anti-scatter grid 612.

The gantry 608 is rotated to cause the x-ray tube 604 and the detector 606 to rotate around the object O while the images are being taken, both with and without the beam stop array 602. Rotation, tilting, and relative linear motion between the gantry 608 and the object O allow any desired data acquisition geometry, including circle, circle plus arc, and circle plus line. Of course, many other data acquisition geometries can be realized, such as circle plus multiple lines, circle plus multiple arcs, spiral, and 360°×integer. As a further alternative, two short arc orbits can be mounted on the gantry 608, one for the x-ray tube 604 and one for the detector 606, so that arc projections can be taken without the need to tilt the gantry 608.

The 2-D detector 606 can be any suitable detector. A preferred example of such a detector has a dynamic range equal to or greater than 1000:1 and an image lag of less than 10%, for example a selenium thin film transistor (STFT) array or a silicon STFT array, in order to provide 2-D projections that correspond to an x-ray attenuation signal pattern. The x-ray source 604 and the 2-D detector 606 are mounted on the gantry frame 608 in such a manner that they both move synchronously.

The cone-shaped beam of radiation X generated by the x-ray source 604 is projected through the body or object O under test. The 2-D detector 606 measures the radiation transmitted along the set of beam paths across the cone X.

Alternatively, a continuous series of two-dimensional detectors (not shown) can be fixedly mounted proximate to the gantry frame 608 and the x-ray source 604 is mounted to the gantry frame such that, upon rotation of the gantry frame, the cone-shaped radiation beam X is projected through the body O under test and sequentially received by each of the series of detectors.

The apparatus 600 or 600' operates under the control of a system control computer 604. The output signals from the detector 606 go to an image processing computer 616 to perform software scatter correction in accordance with the technique disclosed above. The image processing computer 616 may, for example, be comprised of an ULTRA SPARC-1 model workstation, available from Sun Microsystems, Inc. of Mountain View, Calif. 94043.

While a preferred embodiment of the present invention has been set forth in detail, those skilled in the art who have reviewed the present disclosure will readily appreciate that other embodiments can be realized within the scope of the present invention. For example, the images used in SCA can be taken by any suitable equipment. Also, any suitable algorithm for the spatial and temporal interpolations can be used. Therefore, the present invention should be construed as limited only by the appended claims.

I claim:

1. A method for imaging an object while correcting for scatter, the method comprising:

(a) providing a source of imaging radiation, a beam compensation filter, an antiscatter grid, a detector for the imaging radiation, an air gap between the object and the detector and a beam stop array;

(b) moving the source and the detector around the object;

(c) taking a first sequence of images of the object at selected different projection angles while the source and the detector are being moved around the object, to obtain samples of scatter distribution in each of the first sequence of images, by using the source, the beam compensation filter, the beam stop array, the air gap between the object and the detector, the antiscatter grid, and the detector, the first sequence of images comprising N' images;

(d) taking a second sequence of images of the object at different projection angles by using the source and the detector without the beam stop array, the second sequence of images comprising N images, N≧N';

(e) performing a projection angular interpolation on the first sequence of images of the object to obtain a sequence of scatter images, the sequence of scatter images comprising N images, each corresponding to one of the N images of the second sequence of images; and (f) obtaining a sequence of primary images, the sequence of primary images comprising N images, each formed in accordance with a corresponding one of the N images of the second sequence of images and a corresponding one of the N images of the sequence of scatter images.

2. The method of claim 1, wherein step (e) comprises:

(i) recovering the scatter distribution in each of the first set of images so as to obtain a sequence of scatter sample images; and (ii) performing the projection angular interpolation on the sequence of scatter sample images to obtain the sequence of scatter images.

3. The method of claim 2, wherein step (e)(i) comprises performing spatial interpolation on each of the first set of images of the object.

4. The method of claim 3, wherein each of the spatial interpolation and the projection angular interpolation comprises any interpolation methods including a cubic spline interpolation.

5. The method of claim 2, wherein step (e)(i) comprises performing a convolution operation on each of the first set of images of the object.

6. The method of claim 5, wherein the projection angular interpolation is performed through a convolution operation with a selected convolution kernel.

7. The method of claim 1, wherein step (f) comprises subtracting each of the N images of the sequence of scatter images from a corresponding one of the N images of the second sequence of images.

8. The method of claim 1, wherein the imaging radiation is x-ray radiation.

9. The method of claim 8, wherein the imaging radiation is a cone beam of said x-ray radiation.

10. The method of claim 9, further comprising (g) using the sequence of primary images to construct a cone-beam volume computed tomography image.

11. The method of claim 1, wherein N' is equal or greater than 1.

12. The method of claim 1, wherein the angular interval is no greater than 360 degrees.

13. The method of claim 1, wherein the beam compensation filter is a bow-tie filter.

14. A system for imaging an object while correcting for scatter, the system comprising:
   a source of imaging radiation;
   a beam compensation filter;
   an antiscatter grid;
   a detector for the imaging radiation, the detector being so located as to leave an air gap between the object and the detector;
   a beam stop array for being placed, at selected times, in a path of the imaging radiation between the source and the detector;
   a gantry frame for rotating the source and the detector around the object;
   a control device for controlling the gantry, the source and the detector for:
      (i) controlling the source and the detector to rotate around the object while taking a first sequence of images of the object at selected different projection angles by using the source, the detector and the beam stop array, the first sequence of images comprising N' images;
      (ii) controlling the source and the detector to rotate around the object while taking a second sequence of images of the object at different projections angles by using the source and the detector without the beam stop array, the second sequence of images comprising N images, N≧N'; and
   an image processing device, receiving an output of the detector, for:
      (i) performing an angular interpolation on the first sequence of images of the object to obtain a sequence of scatter images, the sequence of scatter images comprising N images, each corresponding to one of the N images of the second sequence of images; and
      (ii) obtaining a sequence of primary images, the sequence of primary images comprising N images, each formed in accordance with a corresponding one of the N images of the second sequence of images and a corresponding one of the N images of the sequence of scatter images.

15. The system of claim 14, wherein the image processing device obtains the sequence of scatter images by recovering the scatter distribution in each of the first sequence of images to obtain a sequence of scatter sample images and performing the projection angular interpolation on the sequence of scatter sample images to obtain the sequence of scatter images.

16. The system of claim 15, wherein the image processing device recovers the scatter distribution by performing spatial interpolation on each of the first set of images of the object.

17. The system of claim 16, wherein each of the spatial interpolation and the angular interpolation comprises any interpolation methods include a cubic spline interpolation.

18. The system of claim 15, wherein the image processing device recovers the scatter distribution by performing a convolution operation on each of the first set of images of the object.

19. The system of claim 18, wherein the projection angular interpolation is performed through a convolution operation with a selected convolution kernel.

20. The system of claim 14, wherein the image processing device obtains the sequence of primary images by subtracting each of the N images of the sequence of scatter images form a corresponding one of the N images of the second sequence of images.

21. The system of claim 14, wherein the imaging radiation is x-ray radiation.

22. The system of claim 21, wherein the imaging radiation is a cone beam of said x-ray radiation and the detector is a two dimensional area detector.

23. The system of claim 22, wherein the image processing device uses the sequence of primary images to construct a cone-beam volume computed tomography image.

24. The system of claim 14, wherein N' is equal to or greater than 1.

25. The system of claim 14, further comprising a rotatable gantry on which the source and the detector are mounted, and wherein the control device controls the rotatable gantry to move the source and the detector around the object to take the first sequence of images at an angular interval.

26. The system of claim 25, wherein the angular interval is no greater than 360 degrees.

27. The system of claim 14, wherein the beam compensation filter is a bow-tie filter.

28. A method for imaging an object while correcting for scatter, the method comprising:
   (a) providing a source of imaging radiation, a detector for the imaging radiation, and a beam stop array;
   (b) taking a first sequence of images of the object by using the source, the detector and the beam stop array, the first sequence of images comprising N' images;
   (c) taking a second sequence of images of the object by using the source and the detector without the beam stop array, the second sequence of images comprising N images, N>N';
   (d) performing a spatial interpolation on the first sequence of images of the object to obtain a sequence of scatter sample images;
   (e) performing an angular interpolation on the sequence of scatter sample images to obtain a sequence of scatter images, the sequence of scatter images comprising N images, each corresponding to one of the N images of the second sequence of images; and
   (f) obtaining a sequence of primary images, the sequence of primary images comprising N images, each formed in accordance with a corresponding one of the N images of the second sequence of images and a corresponding one of the N images of the sequence of scatter images.

29. The method of claim 28, wherein each of steps (d) and (e) is performed using cubic spline interpolation.

30. The method of claim 28, wherein each of steps (d) and (e) is performed using a convolution kernel.

31. The method of claim 28, wherein step (f) comprises subtracting each image of the sequence of scatter images from a corresponding image of the second sequence of images.

32. A system for imaging an object while correcting for scatter, the system comprising:
- a source of imaging radiation;
- a detector for the imaging radiation;
- a beam stop array;
- a gantry frame on which the source and the detector are mounted;
- a control device for controlling the gantry frame, the source and the detector for:
  - (i) taking a first sequence of images of the object by using the source, the detector and the beam stop array, the first sequence of images comprising N' images; and
  - (ii) taking a second sequence of images of the object by using the source and the detector without the beam stop array, the second sequence of images comprising N images, N>N'; and
- an image processing device, receiving an output of the detector, for:
  - (i) performing a spatial interpolation on the first sequence of images of the object to obtain a sequence of scatter sample images;
  - (iii) performing an angular interpolation on the sequence of scatter sample images to obtain a sequence of scatter images, the sequence of scatter images comprising N images, each corresponding to one of the N images of the second sequence of images; and
  - (iii) obtaining a sequence of primary images, the sequence of primary images comprising N images, each formed in accordance with a corresponding one of the N images of the second sequence of images and a corresponding one of the N images of the sequence of scatter images.

33. The system of claim 32, wherein the image processing device performs the spatial interpolation and the angular interpolation using cubic spline interpolation.

34. The system of claim 32, wherein the image processing device performs the spatial interpolation and the angular interpolation using a convolution kernel.

35. The system of claim 32, wherein the image processing device obtains the primary images by subtracting each image of the sequence of scatter images from a corresponding image of the second sequence of images.

* * * * *